(12) United States Patent
Lee

(10) Patent No.: US 8,584,970 B2
(45) Date of Patent: Nov. 19, 2013

(54) WATER JET MASSAGE APPARATUS

(76) Inventor: Don Goo Lee, Seoul (KR)

( * ) Notice: Subject to any disclaimer, the term of this patent is extended or adjusted under 35 U.S.C. 154(b) by 151 days.

(21) Appl. No.: 13/106,041

(22) Filed: May 12, 2011

(65) Prior Publication Data
US 2012/0018533 A1    Jan. 26, 2012

(30) Foreign Application Priority Data
Jul. 21, 2010   (KR) .................. 10-2010-0070432

(51) Int. Cl.
*B05B 15/00*   (2006.01)

(52) U.S. Cl.
USPC ........................................ 239/289; 239/589.1

(58) Field of Classification Search
USPC .............. 239/289, 290, 291, 398, 416.5, 423, 239/526, 589, 589.1
See application file for complete search history.

(56) References Cited

U.S. PATENT DOCUMENTS

| | | | | |
|---|---|---|---|---|
| 2,438,471 A | * | 3/1948 | Ball | ............................... 239/300 |
| 4,239,129 A | * | 12/1980 | Esposito | .......................... 222/79 |
| 4,254,914 A | * | 3/1981 | Shames et al. | ................. 239/383 |
| 4,797,958 A | * | 1/1989 | Guzzini | .......................... 4/541.2 |
| 5,989,647 A | * | 11/1999 | Remy et al. | .................... 427/446 |
| 6,139,512 A | * | 10/2000 | Ricchio | ............................ 601/55 |

FOREIGN PATENT DOCUMENTS

| | | |
|---|---|---|
| JP | 09084713 A | 3/1997 |
| KR | 1020020079505 A | 10/2002 |
| KR | 1020030030723 A | 4/2003 |
| KR | 200325580 Y1 | 9/2003 |

* cited by examiner

*Primary Examiner* — Davis Hwu

(74) *Attorney, Agent, or Firm* — Sherr & Jiang, PLLC

(57) ABSTRACT

Provided is a water jet massage apparatus. The water jet massage apparatus includes a nozzle and a lamp. The nozzle sprays a mixed water jet including air and water. The lamp is disposed in the nozzle. Here, the mixed water jet is sprayed between the lamp and the nozzle while surrounding the lamp. The lamp emits light in a spray direction of the mixed water jet. The nozzle includes a first nozzle part and a second nozzle part. The first nozzle part has a cylindrical shape and has a plurality of air spray holes along an inner circumferential surface thereof. The second nozzle part is detachably disposed in the first nozzle part and having at least one water spray hole.

12 Claims, 5 Drawing Sheets

WATER JET MASSAGE APPARATUS

CROSS-REFERENCE TO RELATED APPLICATIONS

This U.S. non-provisional patent application claims priority under 35 U.S.C. §119 of Korean Patent Application No. 10-2010-0070432, filed on Jul. 21, 2010, the entire contents of which are hereby incorporated by reference.

BACKGROUND

The present disclosure herein relates to a water jet massage apparatus, and more particularly, to a water jet massage apparatus for jetting water including bubbles to a human body to obtain a massage effect.

Generally, showers installed in public bathing facilities include a head in which a plurality of spray holes are formed in a housing defining a water storage space. Recently, showers that have a single spray hole for spraying a water jet including bubbles to provide a massage effect are being widely used.

A related-art water jet massage shower sprays water at a higher water pressure compared to a typical shower, while the water jet massage shower can provide a massage effect at a certain water pressure using a drop of a water pressure by bubbles in a water jet.

Recently, various kinds of shower apparatuses for massaging specific body parts such as neck, back, leg, and foot, as well as underwater massage shower apparatuses such as bathe pools, are being developed.

SUMMARY

The present disclosure provides a water jet massage apparatus for benefiting physical health through a massage (finger-pressure) effect obtained by spaying water jet including bubbles, and benefiting physical and mental health of a user by promoting psychological stability through a chromatherapy using light emission together with the water jet.

Embodiments of the present invention provide water jet massage apparatuses including: a nozzle spraying a mixed water jet including air and water; and a lamp disposed in the nozzle, wherein: the mixed water jet is sprayed between the lamp and the nozzle while surrounding the lamp; the lamp emits light in a spray direction of the mixed water jet; and the nozzle includes: a first nozzle part having a cylindrical shape and having a plurality of air spray holes along an inner circumferential surface thereof; and a second nozzle part detachably disposed in the first nozzle part and having at least one water spray hole.

In some embodiments, the plurality of air spray holes and the at least one water spray hole may be disposed in a circumferential direction, respectively.

In other embodiments, the first nozzle part may have a water jet spray hole through which the mixed water jet is sprayed. The mixed water jet may be discharged from the water jet spray hole through a space between the inner circumferential surface and an outer circumference of the lamp.

In still other embodiments, the second nozzle part may indirectly support the lamp using a support tube.

In even other embodiments, the support may have a cone shape whose diameter gradually increases from the second nozzle part to the lamp.

In yet other embodiments, the lamp may include a plurality of light sources that simultaneously emit light of the same color.

In further embodiments, the plurality of light sources may sequentially or randomly emit light of a plurality of colors.

In still further embodiments, the plurality of light sources may include light emitting diodes.

In even further embodiments, the nozzle may be pivotably coupled to a nozzle head fixedly installed in bathing facilities.

In yet further embodiments, the nozzle may be connected to the nozzle head via a connector. The connector may include: a connection nut detachably connected to the first nozzle; a ball connector having one end thereof pivotably connected to the connection nut and the other end thereof detachably connected to the nozzle head; and a support nut detachably coupling the ball connector to the connection nut and allowing the ball connector not to be released from the connection nut.

In much further embodiments, the connection nut and the ball connector may communicate with each other to guide water from the nozzle head to the nozzle.

In still much further embodiments, the water jet massage apparatus may be installed on one of a wall, a shower booth, a bathe pool, and a ceiling of bathing facilities.

BRIEF DESCRIPTION OF THE DRAWINGS

The accompanying drawings are included to provide a further understanding of the present invention, and are incorporated in and constitute a part of this specification. The drawings illustrate exemplary embodiments of the present invention and, together with the description, serve to explain principles of the present invention. In the drawings.

DETAILED DESCRIPTION OF THE EMBODIMENTS

Exemplary embodiments of the present invention will be described below in more detail with reference to the accompanying drawings. The present invention may, however, be embodied in different forms and should not be construed as limited to the embodiments set forth herein. Rather, these embodiments are provided so that this disclosure will be thorough and complete, and will fully convey the scope of the present invention to those skilled in the art.

Hereinafter, exemplary embodiments of the present invention will be described in detail with reference to the accompanying drawings.

Figure 1:
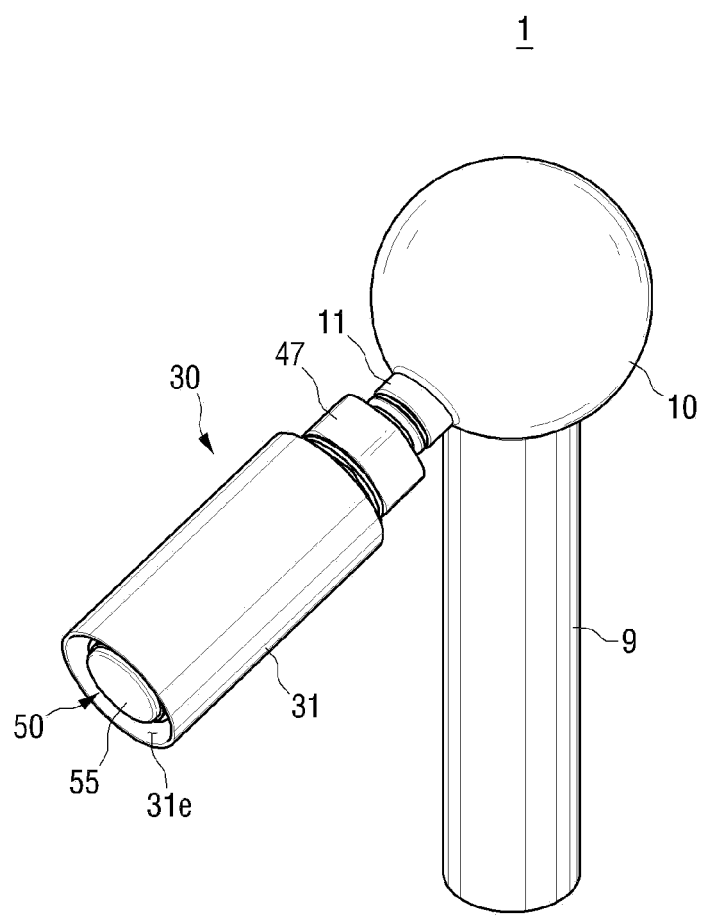
FIG. 1 is a perspective view illustrating a water jet massage apparatus according to an embodiment of the present invention.
Figure 2:
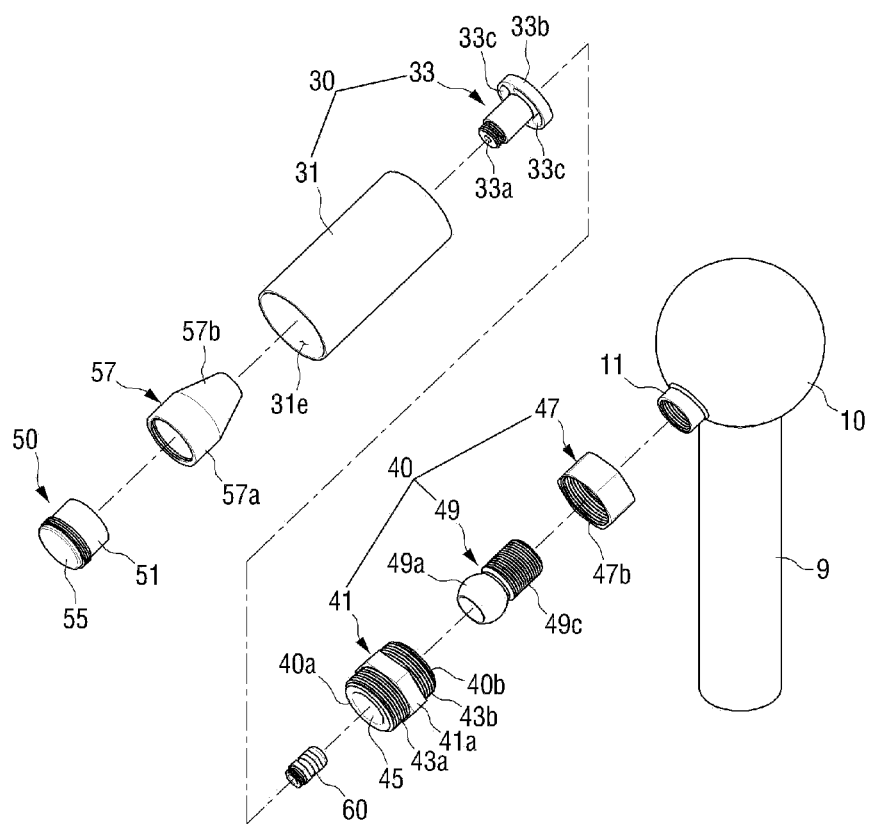
FIG. 2 is an exploded perspective view illustrating a water jet massage apparatus according to an embodiment of the present invention.
Figure 3:
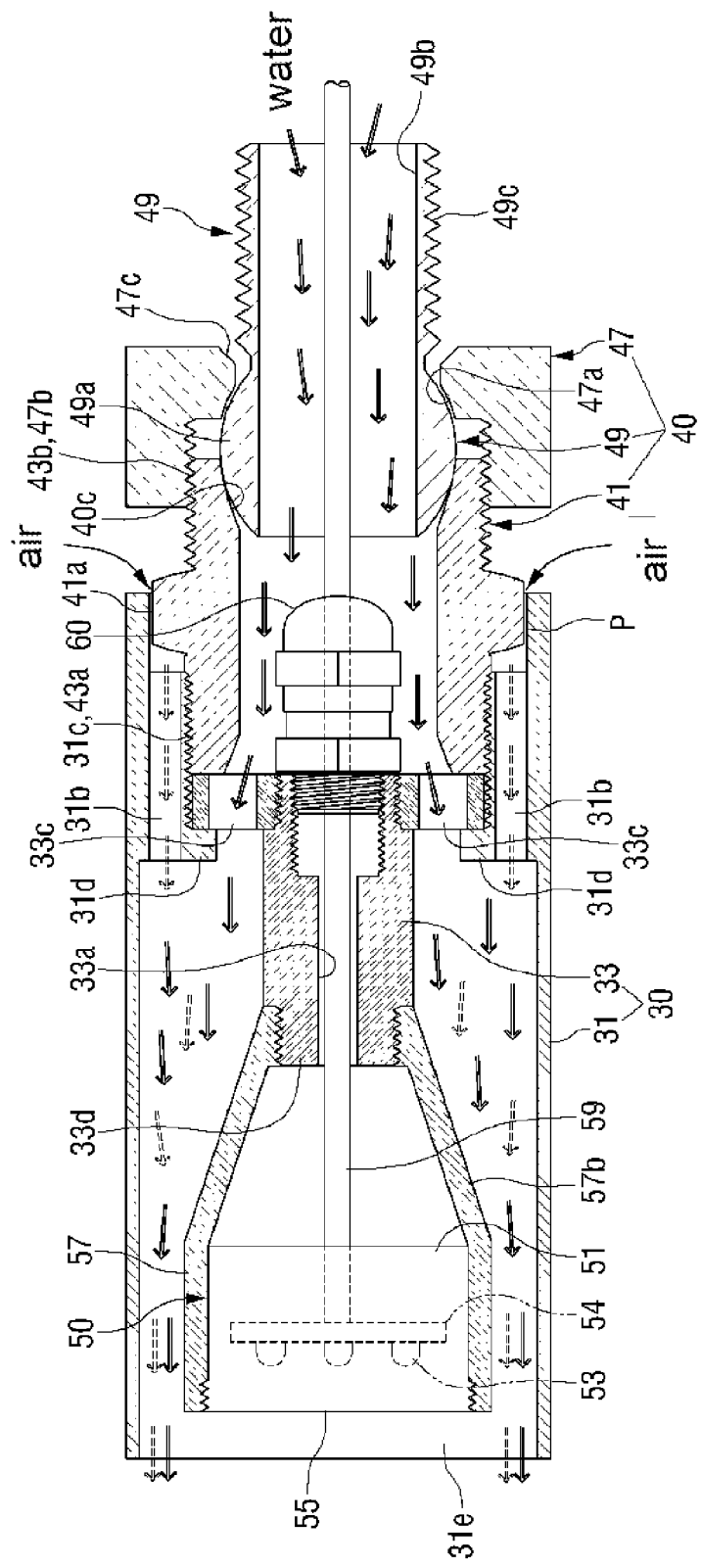
FIG. 3 is a cross-sectional view illustrating the inside of a water jet massage apparatus according to an embodiment of the present invention.

Referring to FIGS. 1 and 2, a water jet massage apparatus 1 may include a nozzle head 10, a nozzle 30, a connector 40, and a lamp 50.

The nozzle head 10 may be connected to a supply pipe 9 installed on a wall, a shower booth, or a bathe pool, and may guide water from a water supply tank (not shown) to the nozzle 30.

The nozzle 30 may be pivotably connected to the upper end of the nozzle head 10 so as to spray water at various angles, and may spray water jet including bubbles such that the sprayed water jet does not cause a pain on a part of a human body hit by the water jet. The nozzle 30 may include a first nozzle part 31 and a second nozzle part 33.

Figure 4:
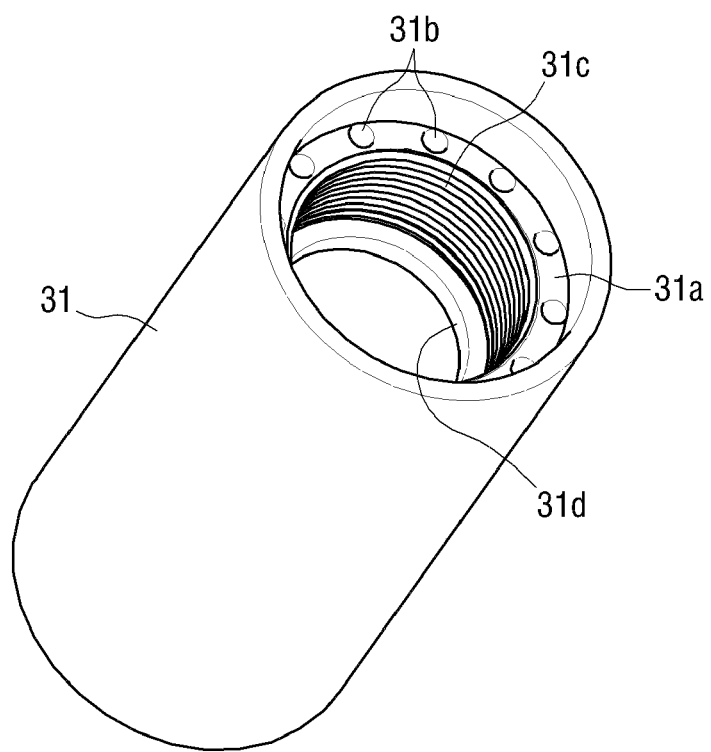
FIG. 4 is a perspective view illustrating a first nozzle part shown in FIG. 3.
Figure 5:
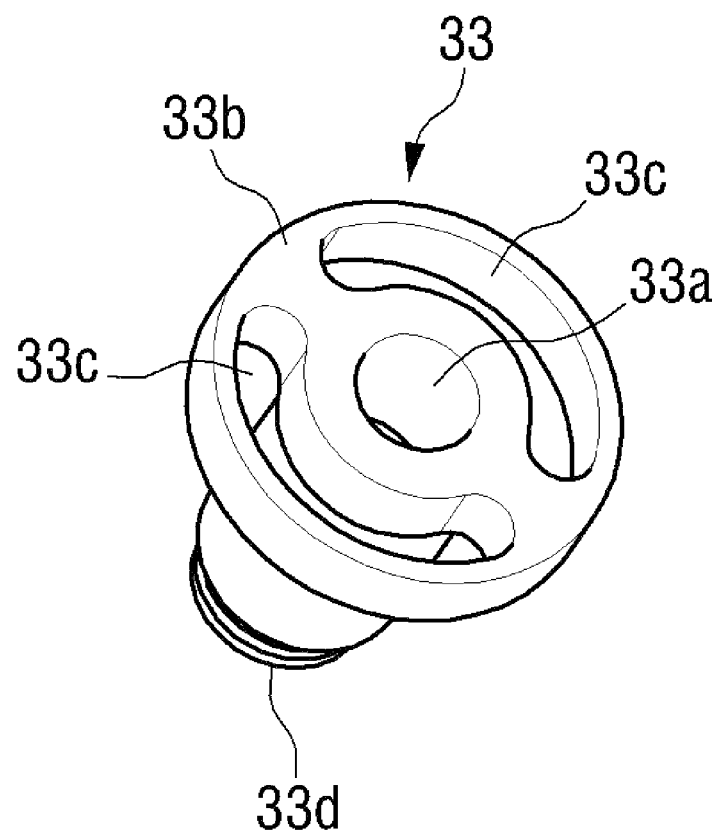
FIG. 5 is a perspective view illustrating a second nozzle part shown in FIG. 3.

Referring to FIG. 4, the first nozzle part 31 may have a substantially cylindrical shape. A block 31a may be protrusively formed along the inner circumferential surface of the rear side of the first nozzle part 31. A plurality of air spray holes 31b may be formed through the block 31a.

In this case, when water passes through the first nozzle part 31 at a certain speed, the internal pressure of the first nozzle part 31 become lower than the atmospheric pressure. Accordingly, due to a difference in pressure between the inside and outside of the first nozzle part 31, external air outside the first nozzle part 31 may flow into the plurality of air spray holes 31b.

Thus, the air flown into the first nozzle part 31 through the air spray hole 31b may be mixed with the water passing through the first nozzle part 31 to be sprayed from the first nozzle part 31 through a water jet spray hole 31e formed in the front end of the first nozzle part 31.

A thread 31c for coupling a connection nut 41 may be formed on the inner circumference of the block 31a. A fixing projection 31d may be formed on the front end of the block 31a to fix the second nozzle part 33.

The second nozzle part 33 may be disposed in the first nozzle part 31, and may have a through hole 33a through which an electric wire 59 is connected from the nozzle head 10 to the lamp 50.

A flange 33b may be formed on the rear end of the second nozzle part 33. The flange 33b may have a pair of water spray holes 33c around the center of the flange 33b. Although it is described in this embodiment that one pair of water spray holes 33c are formed, the number of water spray holes is not limited thereto. For example, at least one water spray hole may be formed. In this case, the second nozzle part 33 may be connected to the flange 33b by screw coupling. The second nozzle part 33 may also be formed integrally with the flange 33b.

In the second nozzle part 33, the flange 33b may be supported on the inner side by the fixing projection 31d formed on the inner circumference of the block 31a of the first nozzle part 31 and the connection nut 41 that is screwed to the block 31a.

The second nozzle part 33 may extend from the flange 33b to the front end 33d thereof by a certain length such that the second nozzle part 33 is parallel to the axial direction of the first nozzle part 31. In this case, the front end 33d of the second nozzle part 33 may be axially coupled to a support tube 57 for supporting the lamp 50.

The connector 40 may include a connection nut 41, a support nut 47, and a ball connector 49.

The connection nut 41 may have a nut fastening surface 41a along the outer circumferential surface of the center thereof, and threads 43a and 43b at the both sides thereof. Also, the connection nut 4 may have a passage allowing water to pass through. In this case, an air flow passage P may be formed between the nut fastening surface 41a and the inner circumferential surface of the first nozzle part 31. Air may flow to the plurality of air flow holes 31b through the air flow passage P.

The front end 40a of the connection nut 41 may support the flange 33b of the second nozzle part, and the rear end 40b thereof may pivotably support the ball connector 49 in conjunction with the support nut 47.

In this case, curved contact surfaces 40c and 47a may be formed on the inner side of the rear end 40b of the connection nut 41 and the inner side of the support nut 47, respectively. The ball connector 49 may include a ball-shaped connection part 49a and a connection thread part 49c. The ball-shaped connection part 49a may also have a curved surface of the same curvature as those of the curved contact surfaces 40c and 47a of the connection nut 41 and the support nut 47. Accordingly, the connection nut 41 may pivot about the ball connector 49. Since the nozzle 30 coupled to the connection nut 41 can be pivoted at various angles, a user can easily set a spray direction of mixed water jet.

The support nut 47 may have a thread 47b on the front end of the inner circumferential surface thereof. Accordingly, the support nut 47 may be detachably engaged with the thread 43b of the connection nut 41. Also, the support nut 47 may have an inclined surface on the rear end of the inner circumferential surface thereof. The inclined surface 47c may be formed to have various inclination angles to match the angle of the nozzle 30.

The ball connector 49 may be screwed to a connection port of the nozzle head 10, and may have a water passage 49b therein.

The lamp 50 may be disposed in the first nozzle part 31, and may be located at the front side of the second nozzle part 33. The lamp 50 may include a lamp housing 51, a plurality of light emitting diodes (LEDs) 53, and a cover 55.

The lamp housing 51 may be inserted into the front end 57a of the support tube 57. The coupling between the lamp housing 51 and the support 57 may be performed by screw coupling.

The plurality of LEDs 53 may be mounted on a certain printed circuit board (PCB) 54 disposed in the lamp housing 51. The plurality of LEDs 53 may simultaneously emit light of the same color, and may sequentially change the color of light according to a program preset in a controller (not shown).

In this case, the light emitted from the plurality of LEDs 53 may be selected from light of colors that can provide psychological stability and benefit psychological therapy. Accordingly, since a user can undergo chromatherapy while being massaged by the water jet massage apparatus according to the present embodiment, the user can get rid of both physical and mental fatigues.

Also, the plurality of LEDs 53 may receive power from the electric wire 59 inserted into the lamp housing 51.

The cover 55 may be disposed on the lamp housing 51 to protect the plurality of LEDs 53, and may be formed of transparent or semitransparent material to emit light of the LEDs 53 through the water jet spray hole 31e of the first nozzle part 31. In this case, the length of light emitting from the LEDs 53 may reach about 30 cm along the direction of the water jet sprayed from the water jet hole 31e.

Since light emitting from the lamp 50 emits to the outside through water jet, the water jet massage apparatus can produce a variety of light to improve the design aspect, compared to a typical lighting apparatus installed in bathing facilities.

The support tube 57 may be disposed such that the lamp 50 is adjacent to the water jet spray hole 31e of the first nozzle part 31, and may have a cone-shape whose diameter gradually increases from the second nozzle part 33 to the lamp 50.

Accordingly, when a water jet including bubbles passes the first nozzle part 31, the speed of the water jet may increase because it passes a passage narrowed by the support tube 57. This enables the water jet to be sprayed at a certain pressure. Thus, the water jet massage apparatus according to the present embodiment may allow the water jet to be sprayed at a pressure appropriate to provide a massage effect to a user.

The electric wire 59 may be led to the nozzle 30 through the supply pipe 9, the nozzle head 10, and the connector 40, and then may be connected to the PCB 54 of the lamp 50. In this case, the electric wire 59 may be guided to the passage 33a of the second nozzle part 33 while being supported by a wire fixing nut 60 coupled to the side of the flange 33b of the second nozzle part 33.

The wire fixing nut 60 may be coupled in a state where the electric wire 59 is inserted by a press fit. Also, a certain packing or seal string may be disposed between the wire fixing nut 60 and the flange 33b to prevent water passing through the connection nut 41 from flowing into the passage 33a of the second nozzle part 33.

The water jet massage apparatus according to an embodiment of the present invention can provide a painless smooth massage to a user by spraying a water jet including bubbles. In addition, the water jet massage apparatus can also perform a psychological cure by a chromatherapy using light emitting from the plurality of LEDs 53, for example, light that can provide a psychological stability.

It has been described in the present embodiment that a water jet massage apparatus is installed on a wall, a shower booth, or a bathe pool of a bathroom, but embodiments are not limited thereto. For example, the water jet massage apparatus may be installed on the ceiling of bathing facilities.

According to an embodiment of the present invention, a smooth massage effect can be achieved without a pain due to water pressure. Also, a psychological cure can be performed by a chromatherapy using light that is emitted from a lamp and can give psychological stability to a user.

The above-disclosed subject matter is to be considered illustrative and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A water jet massage apparatus comprising:
   a nozzle spraying a mixed water jet comprising air and water; and
   a lamp disposed in the nozzle,
   wherein:
   the mixed water jet is sprayed between the lamp and the nozzle while surrounding the lamp;
   the lamp emits light in a spray direction of the mixed water jet; and
   the nozzle comprises:
   a first nozzle part having a cylindrical shape and having a plurality of air spray holes along an inner circumferential surface thereof; and
   a second nozzle part detachably disposed in the first nozzle part and having at least one water spray hole,
   wherein the first nozzle part has a water jet spray hole through which the mixed water jet is sprayed, and the mixed water jet is discharged from the water jet spray hole through a space between the inner circumferential surface and an outer circumference of the lamp.

2. The water jet massage apparatus of claim 1, wherein the plurality of air spray holes and the at least one water spray hole are disposed in a circumferential direction, respectively.

3. The water jet massage apparatus of claim 1, wherein the second nozzle part indirectly supports the lamp using a support tube.

4. The water jet massage apparatus of claim 3, wherein the support has a cone shape whose diameter gradually increases from the second nozzle part to the lamp.

5. The water jet massage apparatus of claim 1, wherein the lamp comprises a plurality of light sources that simultaneously emit light of the same color.

6. The water jet massage apparatus of claim 5, wherein the plurality of light sources sequentially or randomly emits light of a plurality of colors.

7. The water jet massage apparatus of claim 5, wherein the plurality of light sources comprise light emitting diodes.

8. The water jet massage apparatus of claim 6, wherein the plurality of light sources comprise light emitting diodes.

9. The water jet massage apparatus of claim 1, wherein the nozzle is pivotably coupled to a nozzle head fixedly installed in bathing facilities.

10. The water jet massage apparatus of claim 9, wherein the nozzle is connected to the nozzle head via a connector, and the connector comprises:
    a connection nut detachably connected to the first nozzle;
    a ball connector having one end thereof pivotably connected to the connection nut and the other end thereof detachably connected to the nozzle head; and
    a support nut detachably coupling the ball connector to the connection nut and allowing the ball connector not to be released from the connection nut.

11. The water jet massage apparatus of claim 9, wherein the connection nut and the ball connector communicate with each other to guide water from the nozzle head to the nozzle.

12. The water jet massage apparatus of claim 1, wherein the water jet massage apparatus is installed on one of a wall, a shower booth, a bathe pool, and a ceiling of bathing facilities.

* * * * *